United States Patent [19]

Monk et al.

[11] 3,949,389

[45] Apr. 6, 1976

[54] MOISTURE DETECTOR

[75] Inventors: Kenneth A. Monk, Ormstown; Robert C. Braithwaite, Beaconsfield, both of Canada

[73] Assignee: ITT Industries, Inc., New York, N.Y.

[22] Filed: Oct. 2, 1974

[21] Appl. No.: 510,953

[30] Foreign Application Priority Data

Feb. 28, 1974 Sweden.......................... 7402657

[52] U.S. Cl. .................. 340/235; 340/270; 317/65
[51] Int. Cl.² ...................................... G08B 21/00
[58] Field of Search................ 340/235, 237 R, 270; 200/61.05; 324/65 R; 317/148.5 B

[56] References Cited
UNITED STATES PATENTS

| | | | |
|---|---|---|---|
| 2,323,950 | 7/1943 | Wade............................. | 340/242 X |
| 3,033,023 | 5/1962 | Hooper et al................ | 340/242 UX |
| 3,242,473 | 3/1966 | Shivers, Jr. et al. ................ | 340/235 |
| 3,364,363 | 1/1968 | Iordanidis.................. | 317/148.5 B X |
| 3,469,250 | 9/1969 | Voigt.............................. | 340/237 S |
| 3,781,838 | 12/1973 | Primmer......................... | 340/237 R |

Primary Examiner—John W. Caldwell
Assistant Examiner—Daniel Myer
Attorney, Agent, or Firm—John T. O'Halloran; Menotti J. Lombardi, Jr.; Vincent Ingrassia

[57] ABSTRACT

This invention relates to an apparatus for detecting the presence of a specific concentration of a conducting medium (water) in an insulating medium (oil) wherein the water/oil mixture forms an emulsion containing discrete droplets of water. A probe containing two electrodes, the first of which has a flat surface and the second of which is cone-shaped having a vertex directed at the flat surface, is immersed into the emulsion. A pulsating dc voltage is applied to the first electrode producing a static electrical charge which repels the insulating medium while having no effect on the conducting medium, causing droplets of the conducting medium to migrate towards and accumulate in the area between the electrodes. When a sufficient number of droplets have accumulated, a conductive path is formed between the electrodes causing an alarm to be generated.

13 Claims, 5 Drawing Figures

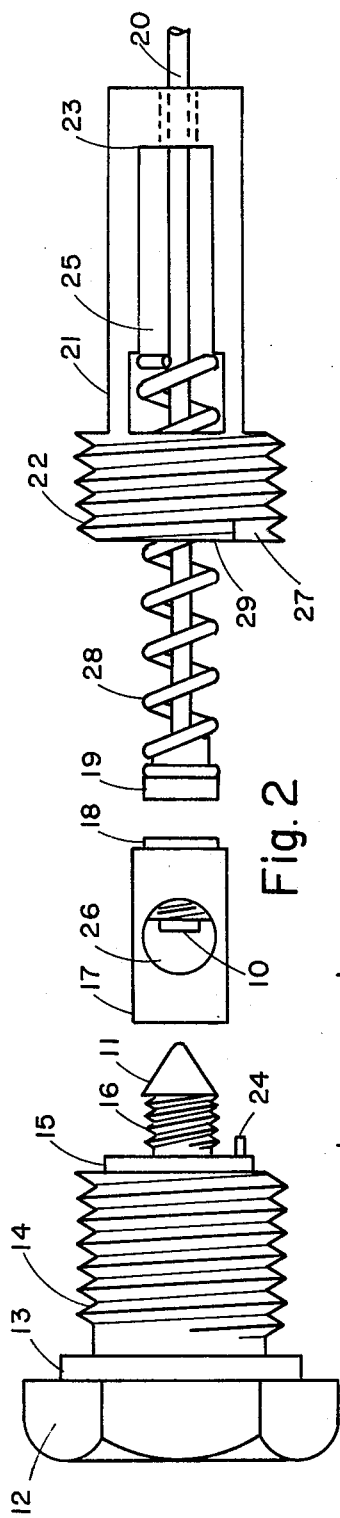
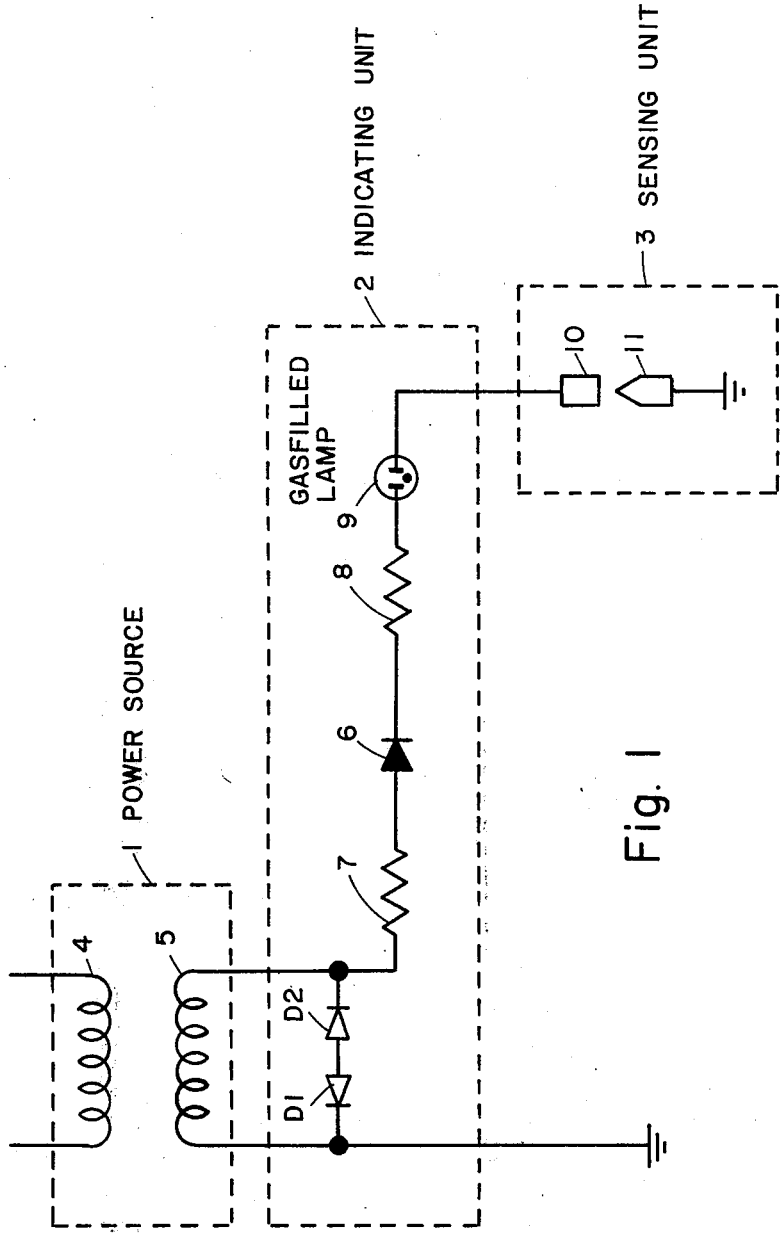

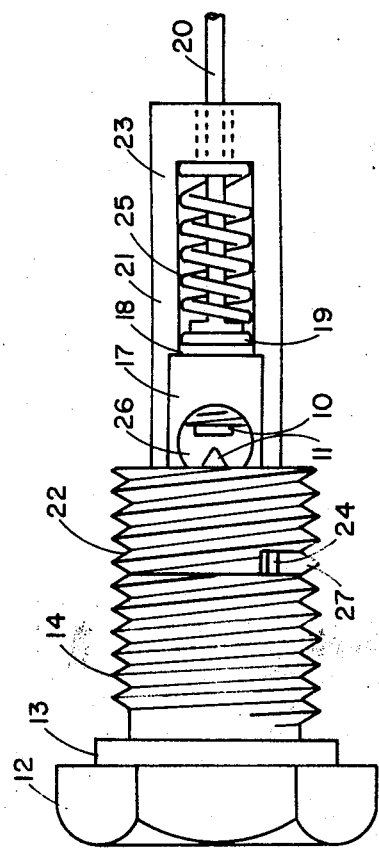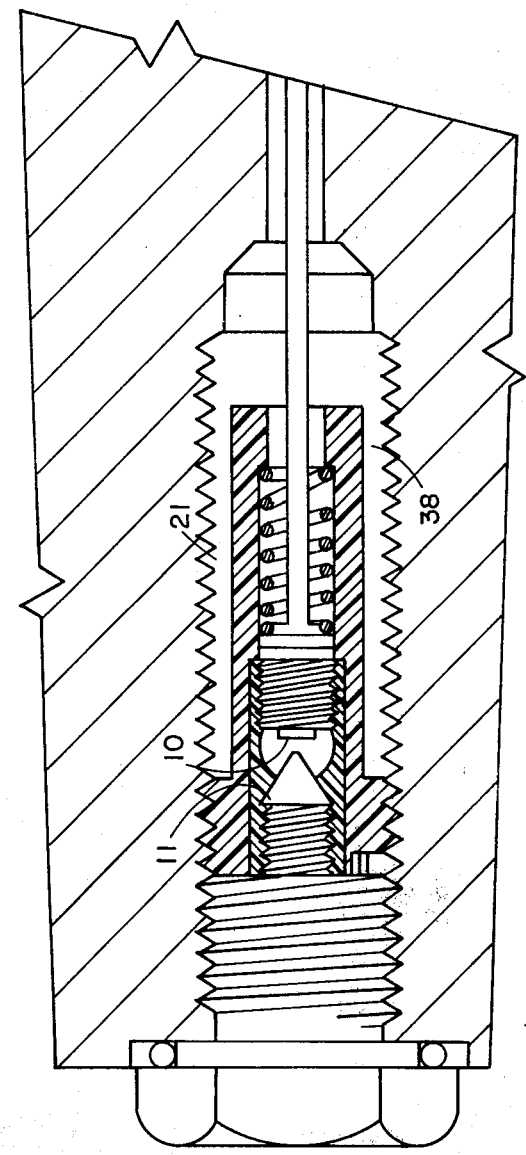

MOISTURE DETECTOR

BACKGROUND OF THE INVENTION

This invention relates to a moisture detector and, more particularly, to the detection of a low percentage of water in the oil housing or stator housing of an electrical submersible pump wherein due to the motion imparted to the oil by the rotating shaft of the pump, the oil/water mixture is in the form of an emulsion.

Electrical submersible pumps have applications in many areas. For example, construction sites, mines, trenches, marine salvage, public works and sewerage treatment. Obviously, water must be prevented from reaching the motor housing of the submersible pumps. To this end, the pumps are generally provided with a plurality of seals which segregates oil in the oil housing from the motor housing and the fluid being pumped. The central rotating shaft of the pump maintains the oil in the oil housing in constant motion. If water were to somehow penetrate the lower seal arrangement and enter the oil housing, the oil/water mixture would become an emulsion apparent by its milky-white color.

In order to determine if any water has penetrated the oil housing, it is common practice to provide an inspection screw which, when removed, allows visual inspection of the oil in the oil housing. This requires removal of the pump from its operating environment and removal of the inspection screw. If a milky-white mixture is observed, it would be apparent to the observer that water has entered the oil housing. It is to be noted, however, that the amount of water in the oil housing cannot be determined from a visual inspection alone.

It has been deemed desirable to provide an automatic device for detecting the presence of water within the oil or stator housing of the pump; however, solutions to this problem have been restricted by certain agencies, such as the Underwriters Laboratories, which have limited the amount of voltage that can be applied to certain devices such as electric submersible pumps. The situation is further complicated by the fact that due to the motion of the oil, water in the oil forms discrete bubbles, each bubble electrically insulated from other bubbles by the oil itself which exhibits dielectric characteristics.

Due to the low voltage requirement, various low-voltage arrangements have been employed, one of which is the provision of a thermistor in the stator housing of the pump. Thermistors are devices which exhibit a change in resistance proportional to a corresponding change in temperature. Therefore, it can be seen that even if oil alone were to enter the stator housiing and make contact with the thermistor, the temperature of the thermistor would decrease and an alarm generated. However, it is well known that a certain amount of oil alone in the stator housing will not damage the motor, but will be burned away. Further, the presence of oil alone in the stator chamber is not uncommon since each time the pump motor is started, the mechanical elements may jump and the seals lifted, thereby allowing a small amount of oil to enter the stator chamber. This results in the generation of an alarm due to the cooling of the thermistor by the oil alone. Since, as stated above, a small amount of oil in the stator chamber represents no great danger, an alarm generated, due to the presence of oil alone, constitutes not only a nuisance, but also a severe reduction of the integrity of the detection system itself. Further, due to the low voltage requirement, it is necessary to provide complex and expensive electronic amplifying components. By adding additional components, the mean time between failure of the detection system is substantially decreased. A further disadvantage of the thermistor approach resides in the sensitivity of the thermistor to thermal ambients in the operational environment of the electrical submersible pump.

A second approach of detecting water in the stator housing of the pump is the basic conductivity approach wherein two steel electrodes are permanently provided in the stator housing. A voltage, typically 12 volts to 24 volts, is provided across the electrodes. When the water content becomes high enough, a conductive path will be formed between the two electrodes, and an alarm signal generated. This arrangement suffers from the same disadvantages as the thermistor approach due to the low voltage requirement, i.e., the requirement of additional complicated electronic amplifying apparatus. Further, before a signal will be generated (before a conductive water path between the electrodes is formed), it is necessary that a very large percentage of water be present, at which time, damage may have already been caused. In an attempt to reduce the percentage of water necessary to generate an alarm, the spacing between probes can be greatly reduced. However, this may lead to accidental conduction between the probes, thereby providing a nuisance effect and severe degradation of the reliability of the detection system.

As stated previously, the conductivity probe is build into the pump, and any malfunction would require disassembly of the pump to retrieve the probe. Further, a wire to each probe is necessary, and as the length of the wires increase, the amount of voltage drop due to the internal resistance of the wires is increased. This reduction in voltage across the probes necessitates the presence of a larger percentage of water in order to form a conductive path between the electrodes and thereby produce a warning signal.

There has been a great deal of discussion regarding the amount of water in the oil housing of the pump which can be tolerated before the situation is deemed critical. It has been stated by some that there must be 50 percent water in oil before the situation becomes critical, while others maintain that a percentage as low as 5 or 10 percent is critical. Irrespective of this, it would be greatly advantageous to be able to detect a very small percentage of water in oil as an indication that a leak does exist, thereby warranting closer surveillance or repair at a very early stage.

Ignoring the other disadvantages of the basic conductivity approach, it will, in all likelihood, provide an alarm or warning if the concentration of water in oil becomes very high. However, at this point, severe damage may have already occurred. Neither the basic conductivity probe approach nor the thermistor approach is suitable for detecting low percentages of water in the oil or stator housing of an electrical submersible pump.

SUMMARY OF THE INVENTION

It is an object of the present invention to provide an apparatus for detecting the presence of water in oil wherein the oil/water mixture is in emulsion form.

It is a further object of the present invention that the device be capable of detecting the presence of emulsified oil and water wherein the percentage of water is as low as 1%.

It is a further object of the present invention that the apparatus provide an alarm when the percentage of water in oil reaches a predetermined level.

It is a further object of the present invention that the device be easily adaptable to the detection of water in the oil or stator housing of an electrical submersible pump.

Finally, it is an object of the present invention that the device be a low current device (3 ma or less) whereby the safety of personnel who must necessarily handle the pump is not compromised.

According to a broad aspect of the invention there is provided a moisture detector comprising: a source of pulsating dc voltage; a first electrode having applied thereto said pulsating dc voltage; a second electrode coupled in close proximity to said first electrode and coupled to ground whereby a static electrical discharge occurs when sufficient moisture is present between said first and second electrodes to form a conductive path between said first and second electrodes; and means for generating an alarm when said conductive path is formed.

According to a further aspect of the invention, there is provided an apparatus for detecting the presence of a specific concentration of a conducting medium in an insulating medium wherein the conducting/insulating medium mixture is in the form of an emulsion containing discrete droplets of said conducting medium, comprising: a source of pulsating dc voltage; a first electrode immersed in said emulsion and having applied thereto said pulsating dc voltage whereby a static electrical charge is formed on said first electrode which repels said insulating medium while having no effect on said conducting medium, causing droplets of said conducting medium to migrate towards, and accumulate in, the area around said first electrode; a second electrode coupled to ground and immersed in said emulsion, said second electrode positioned in close proximity to said first electrode such that a static electrical discharge occurs when a sufficient number of droplets of said conducting medium accumulates between said first and second electrodes to form a conductive path; and means for generating an alarm when said conductive path is formed.

According to still a further aspect of the invention there is provided a probe for use in an apparatus which detects the presence of a conducting medium in an insulating medium wherein said probe is inserted into an aperture in a housing containing the conducting/insulating medium mixture comprising: a first cone-shaped electrode having a vertex and a longitudinal axis; a second electrode having a substantially flat surface in a plane perpendicular to said longitudinal axis; and an insulating connector for housing said first and second electrodes and positioning said first and second electrodes such that said vertex is directed at said flat surface and is in close proximity thereto and electrically isolated therefrom, said connector having an aperture therein to allow said mixture to flow freely in an area between said first and second electrodes.

The above and other objects of the present invention will be more clearly understood from the following detailed description taken in conjunction with the accompanying drawings, in which:

BRIEF DESCRIPTION OF THE DRAWINGS

FIG. 1 is a schematic diagram of the inventive moisture detector;

FIG. 2 is a drawing of a disassembled sensing unit according to FIG. 1;

FIG. 3 is a drawing of an assembled sensing unit according to FIG. 2;

FIG. 4 shows the assembled sensing unit of FIG. 3 threaded into a hole provided for an inspection screw.

DESCRIPTION OF THE PREFERRED EMBODIMENT

Figure 5:
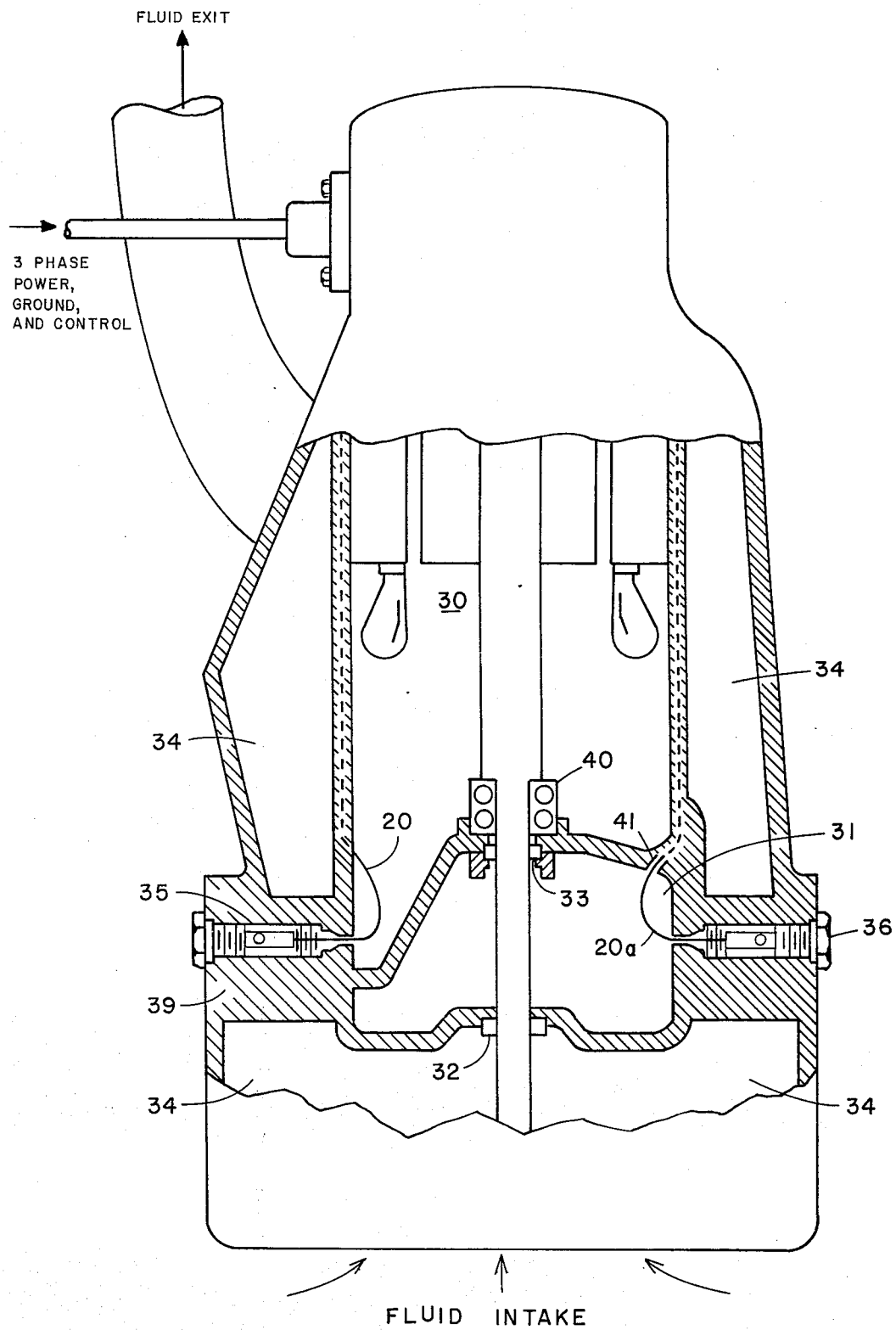
FIG. 5 is a cross-sectional view of an electrical submersible pump having inserted therein sensing units of the type shown in FIG. 2.

As stated previously, the invention is primarily concerned with the situation where water has entered an oil chamber wherein the oil, due to some external force acting upon it, is in constant motion. This results in a homogenized mixture of water and oil, wherein the water in the water/oil mix forms discrete droplets. Oil, being a dielectric material, insulates the water droplets from each other; however, the presence of water droplets in the oil reduces the dielectric strength of the oil.

FIG. 1 is a schematic diagram of an apparatus for detecting low concentrations of water in an oil/water emulsion of the type described above. The device comprises three main units: a power source 1, an indicating unit 2, and a sensing unit 3. The power source contains a step-up isolating transformer having a primary winding coupled to an ac source, typically 120 volts, and a secondary isolated winding for producing 200 to 240 volts at 50/60 Hz.

The indicating unit comprises a diode 6 which produces at its ouput a half-wave rectified dc voltage. Also included in the indicating unit 2 are resistors 7 and 8, resistor 8 being the internal resistance of a gas-filled indicator lamp 9. The purpose of resistors 7 and 8 is to reduce the current to a level which is not dangerous to man, typically below 3ma. Two selenium rectifiers D1 and D2 are provided in a back-to-back arrangement across the secondary winding to dissipate any stray or spurious ac voltages which might trigger the lamp.

The sensing unit 3, which is inserted into the oil/water emulsion, comprises two electrodes 10 and 11. Striker electrode 10 is coupled in series with lamp 9, resistors 7 and 8, and diode 6. Electrode 11 has a cone-shaped portion with a rounded tip directed at the striker electrode and is coupled to ground.

The operation of the device is as follows: The half-wave rectified voltage produced by diode 6 is applied through lamp 9 to striker electrode 10, resulting in a pulsating static electrical discharge (corona effect) by striker 10. The vertex of electrode 11, hereinafter referred to as the anvil, is directed at the striker electrode and defines the path that a subsequent static discharge would take. The presence of oil between the striker 10 and the anvil 11 creates an insulation between the striker and anvil that cannot be broken down by the corona effect. However, the static electrical charge repels the insulating medium (oil) while having no effect on the conducting medium (water). Due to this repelling effect of the oil molecules by the static charge, there is created a pulsing electrical pressure in the oil which results in slight movement or turbulence. The turbulence is increased by the pulsing effect caused by rectification of the ac signal. As the oil molecules are repelled, the turbulence causes an electrostatic collection of water droplets between the striker 10 and anvil 11. When a sufficient number of water droplets accumulate, conductivity columns of water establish a path between the striker and anvil, and sensing unit 3 becomes conductive. At this point, the lamp 9 ignites and will remain ignited even though series resistors 7 and 8 reduce the current to under 3ma for safety purposes. Other indicating or alarm circuits may be used and/or coupled to the indicating system.

It should now be clear in view of the above that by adjusting the spacing between the striker 10 and anvil 11, an alarm will be generated when a specific predetermined percentage of water is present in the oil. Further, if the spacing between the striker and anvil is set to detect a specific percentage of water in oil, an alarm will not be generated unless the concentration of water has reached that level, even though the electrostatic migration effect is continually occurring. For example, if the gap is set to detect 15 percent water and there exists an oil/water emulsion containing 10 percent oil, the static discharge will cause the electrostatic migration of water droplets towards the area between the striker 10 and anvil 11. However, the surface tension of the water opposes the electrostatic migration, preventing the formation of the above described conducting columns. The gap is set such that the electric field will not be sufficient to overcome the surface tension of the water unless the percentage of water is equal to or greater than the percentage for which the gap has been spaced.

In some cases, it may be desirable to employ several such devices, each having a gap set to detect a different water content. For example, a first device may be set to generate an alarm (green light) when the content of water in the mixture has reached 5 percent. A second device may provide an alarm (blue light) when the amount of water has reached 15 percent. Assuming that the critical percentage is greater than 15 percent, each of the above described alarms indicate, with a varying degree of urgency, the possibility of serious future damage. A third device may be employed to provide an alarm when the water level has reached 50 percent. This, in turn, could be employed to actuate a relay and thereby disconnect power to the motor before serious damage occurs.

A practical application of the inventive moisture detector will now be described with respect to its use in an electrical submersible pump. As stated previously, one of the most common methods of determining if water has penetrated the oil or stator chamber of an electrical submersible pump is to remove one of several inspection screws and visually monitor the oil to determine if it has become milky-white, indicating the presence of water. The sensing unit 3, shown in FIG. 1, has been designed to be accommodated by the threaded holes provided for standard inspection screws.

FIG. 2 illustrates the sensing unit in disassembled form containing a striker 10 and anvil 11. The component part of the sensing unit 3 to which the anvil 11 is fixed is similar to the inspection screw itself; however, it is much shorter. It comprises a screw head 12, a shoulder 13, and a threaded portion 14. Coupled to flat surface 15 of threaded portion 14 and on a common axis therewith is a second smaller threaded portion 16 having a conical tip comprising the anvil of the sensing unit.

The next component, which houses the striker electrode, comprises a hollow internally-threaded cylinder 17 made of an insulating plastic, such as teflon. The striker electrode 10 is also in the form of a threaded screw having a head 18. Cylinder 17 may then be screwed onto threaded portion 16, bringing the striker electrode 10 into close proximity with anvil 11. Since the striker electrode 10 is also threaded, the spacing between the striker electrode and anvil may be adjusted by rotating the head 18 of striker 10. Cylinder 17 electrically isolates anvil 11 from striker 10.

Next, there is provided a contact element 19 electrically coupled to lead 20. Surrounding lead 20 is a spring 28 which forces contact 19 against the head 18 of striker 10 when the probe is completely assembled.

Housing 21, again made of an insulating plastic material impervious to oil and water, such as teflon, comprises a threaded portion 22 having a small hole 27 therein which engages pin 24 on threaded portion 14 when the device is assembled. In this way, housing 21 will be positioned such that a continuous and uninterrupted threaded body comprising threaded portions 14 and 22 will be formed. When assembled, the end of spring 28 opposite contact 19 engages lip 23 of plastic component 21, thereby forcing contact 19 against head 18 of striker 10.

FIG. 3 illustrates the sensing unit in its assembled state with like numerals denoting like elements. It can be seen in FIG. 3 that the gap between anvil 11 and striker 10 is visible through opening 25 in plastic element 21 and opening 26 in plastic cylinder 17.

FIG. 4 shows the sensing device inserted into a space provided for a standard inspection screw. The sensing device is merely screwed into an internally threaded hole provided in a pump housing 39. Due to the configuration of the device the contents of the chamber to which the inspection screw would lead is free to circulate in the area 38 around the striker 10 and anvil 11.

To complete the discussion of the application of the inventive moisture detector for use in electrical submersible pumps, a basic pump configuration is shown in FIG. 5. The areas of interest are stator chamber 30, oil chamber 31, seal 32, seal 33, and bearing 40. Also shown in the drawing are those areas 34 which come into contact with water during normal operation. Also shown are two sensing units 35 and 36 of the type described hereinabove. Sensing unit 35 is positioned to monitor the stator chamber, while sensing unit 36 is positioned to detect the presence of water in the oil chamber. Leads 20 and 20a, coupled to the sensing units 35 and 36 respectively, are merely run upward and along the pump housing to an area of the pump housing where electrical contact is made with the remainder of the circuit shown in FIG. 1. An oil grommet 41 is provided for the passage of lead 20a from the oil housing to the stator housing.

Since most pumps are provided with a plurality of inspection screws, it should now be appreciated that a number of sensing units could be employed, each having gaps prespaced to provide alarms at various predetermined levels of water in oil. It should further be appreciated that the device can be easily inserted or removed without requiring disassembly of the pump, as is the case when standard conductivity probes are employed. Further, it is not inconceivable that instead of manually rotating head 18 of striker 10 to vary the spacing between striker and anvil, thereby changing the threshold at which an alarm will be generated, the plastic cylinder 17, having the striker mounted therein, could be constructed to detect one particular percentage of water in oil. For example, a user may be supplied with a plurality of cylinders 17 containing strikers 10, each designed to detect a particular percentage of water in oil. Therefore, if the user desires to detect the presence of 15 percent water in oil, as opposed to 5 percent water in oil, the user may merely remove that portion of the sensing unit on which cylinder 17 and striker 10 is fixed, remove the cylinder in use, and replace it with one which may be premarked 15 percent.

What has been provided is a simple and inexpensive device which will detect the presence of water in oil at any desired percentage level between 1 and 50 percent which eliminates the above described disadvantages encountered when using the thermistor or standard conductivity probe approach.

While the principles of the invention have been described above in connection with specific apparatus, it is to be clearly understood that this description is made only by way of example and not as a limitation on the scope of the invention.

What is claimed is:

1. An apparatus for detecting the presence of a specific concentration of a conducting medium in an insulating medium wherein the conducting/insulating medium mixture is in the form of an emulsion containing discrete droplets of said conducting medium, comprising:
   a source of pulsating dc voltage;
   a first electrode having a substantially flat surface, said first electrode immersed in said emulsion and having applied thereto said pulsating dc voltage whereby a static electrical charge is formed on said first electrode which repels said insulating medium while having no effect on said conducting medium, causing droplets of said conducting medium to migrate towards, said accumulate in, the area around said first electrode;
   a second cone-shaped electrode having a vertex directed at said flat surface, said flat surface in a plane substantially perpendicular to the longitudinal axis of said second electrode, said second electrode coupled to ground and immersed in said emulsion, said second electrode positioned in close proximity to said first electrode such that a static electrical discharge occurs when a sufficient number of droplets of said conducting medium accumulates between said first and second electrodes to form a conductive path; and
   means for generating an alarm when said conductive path is formed.

2. An apparatus according to claim 1 further including means coupled across said source for dissipating spurious ac signals.

3. An apparatus according to claim 1 further including means for adjusting the spacing between said first and second electrodes to render said detecting apparatus responsive to a particular concentration of conducting medium in said insulating medium.

4. An apparatus according to claim 3 wherein said means for producing said pulsating DC voltage is a half-wave rectifier.

5. An apparatus according to claim 4 further including current limiting means coupled to said DC source for maintaining the current below a predetermined level.

6. An apparatus according to claim 5 wherein said current limiting means comprises at least one resistor.

7. An apparatus according to claim 6 wherein said generating means is a gas-filled lamp.

8. In an apparatus for detecting the presence of a specific concentration of water in oil wherein the oil/water mixture is in the form of an emulsion containing discrete droplets of water, the combination comprising:
   a source of ac power;
   a half-wave rectifier coupled to said source for producing a pulsating ac voltage;
   at least one resistor coupled in series with said half-wave rectifier for maintaining the current below a predetermined level;
   a first electrode immersed in said emulsion and having applied thereto said pulsating dc voltage, forming a static charge thereon which repels the oil while having no effect on said water droplets, causing said water droplets to migrate towards, and accumulate in, the area around said first electrode, said first electrode having a substantially flat surface in a plane perpendicular to the longitudinal axis of said first electrode;
   a second electrode coupled to ground and immersed in said emulsion in close proximity to said first electrode such that a static electrical discharge occurs when a sufficient number of water droplets accumulate between said first and second electrodes to form a conductive path, said second electrode being substantially cone-shaped and having a vertex directed at said flat surface for defining a path which said static discharge will take;
   means for generating an alarm when said conductive path is formed; and
   means for adjusting the spacing between said first and second electrodes to render said detecting apparatus responsive to a particular concentration of water in oil.

9. A probe for use in an apparatus which detects the presence of a conducting medium in an insulating medium wherein said probe is inserted into an aperture in a housing containing the conducting/insulating medium mixture comprising:
   a first cone-shaped electrode having a vertex and a longitudinal axis;
   a second electrode having a substantially flat surface in a plane perpendicular to said longitudinal axis;
   an insulating connector for housing said first and second electrodes and positioning said first and second electrodes such that said vertex is directed at said flat surface and is in close proximity thereto and electrically isolated therefrom, said connector having an aperture therein to allow said mixture to flow freely in an area between said first and second electrodes;
   metal base means comprising: an externally threaded section; and means fixedly coupled to said section whereby rotation of said means causes rotation of said externally threaded section, said first electrode fixedly coupled to said base means;
   a substantially cylindrical insulating housing having apertures therein, one end of said insulating housing engaging said base means and surrounding said insulating connector;
   a terminal plate housed within said insulating housing and resiliently urged against said second electrode when said insulating housing engages said base; and
   a lead wire having one end electrically coupled to said terminal plate, said lead wire exiting through one of said apertures in said insulating housing for making electrical contact with said apparatus.

10. A probe according to claim 9 wherein said first electrode has an externally threaded portion, said second electrode has an externally threaded portion, and said insulating connector is internally threaded whereby said first and second electrodes may be screwed into said insulating connector.

11. A probe according to claim 9 further including means for adjusting the spacing between said first and second electrodes.

12. A probe according to claim 11 wherein said insulating housing has an externally threaded section which cooperates with the threaded section of said base means to form a continuous threaded body which can be screwed into an internally threaded housing.

13. A probe according to claim 12 wherein said insulating housing contains a spring for forcing said terminal plate against said second electrode.

* * * * *

UNITED STATES PATENT OFFICE
CERTIFICATE OF CORRECTION

PATENT NO. : 3,949,389
DATED : April 6, 1976
INVENTOR(S) : K. Monk-R.C. Braithwaite It is certified that error appears in the above-identified patent and that said Letters Patent are hereby corrected as shown below:

Column 7, line 35, before "accumulate"

Delete "said" and substitute therefor -- and --.

Signed and Sealed this

Third Day of August 1976

[SEAL]

Attest:

RUTH C. MASON
*Attesting Officer*

C. MARSHALL DANN
*Commissioner of Patents and Trademarks*